(12) United States Patent
Schindhelm et al.

(10) Patent No.: US 8,844,525 B2
(45) Date of Patent: Sep. 30, 2014

(54) METHOD AND APPARATUS FOR DETECTING AND TREATING HEART FAILURE

(75) Inventors: Klaus Henry Schindhelm, Glenhaven (AU); Ian Wilcox, Dawes Point (AU); Rachel Ann Coxon, Rosehill (AU)

(73) Assignee: ResMed Limited (AU)

( * ) Notice: Subject to any disclaimer, the term of this patent is extended or adjusted under 35 U.S.C. 154(b) by 1166 days.

(21) Appl. No.: 12/483,357

(22) Filed: Jun. 12, 2009

(65) Prior Publication Data
US 2010/0018530 A1 Jan. 28, 2010

Related U.S. Application Data

(60) Provisional application No. 61/083,596, filed on Jul. 25, 2008.

(51) Int. Cl.
| | |
|---|---|
| *A61M 16/00* | (2006.01) |
| *A61B 5/087* | (2006.01) |
| *A61B 5/0205* | (2006.01) |
| *A61B 5/08* | (2006.01) |
| *A61M 16/06* | (2006.01) |

(52) U.S. Cl.
CPC .............. *A61B 5/0816* (2013.01); *A61B 5/087* (2013.01); *A61M 2016/0021* (2013.01); *A61B 5/0205* (2013.01); *A61M 16/0069* (2014.02); *A61M 2230/06* (2013.01); *A61M 2230/202* (2013.01); *A61M 2230/30* (2013.01); *A61M 16/0666* (2013.01); *A61M 2230/205* (2013.01); *A61M 16/0051* (2013.01); *A61M 2205/3592* (2013.01); *A61M 2016/0036* (2013.01); *A61M 2205/502* (2013.01); *A61M 2205/3561* (2013.01); *A61M 2230/63* (2013.01); *A61M 2205/18* (2013.01); *A61M 2205/3584* (2013.01); *A61M 2230/04* (2013.01)
USPC ............. 128/204.23; 128/204.22; 128/204.26

(58) Field of Classification Search
USPC .............. 128/204.21–204.23, 204.26, 205.23
See application file for complete search history.

(56) References Cited

U.S. PATENT DOCUMENTS

| | | | |
|---|---|---|---|
| 4,519,399 A | 5/1985 | Hori | |
| 5,020,516 A | 6/1991 | Biondi et al. | |

(Continued)

FOREIGN PATENT DOCUMENTS

| | | |
|---|---|---|
| EP | 1295623 A1 | 3/2003 |
| GB | 2294642 A | 5/1996 |

(Continued)

OTHER PUBLICATIONS

European Search Report, EP 09166164, dated Oct. 7, 2009.

(Continued)

*Primary Examiner* — Lynne Anderson
(74) *Attorney, Agent, or Firm* — Lerner, David, Littenberg, Krumholz & Mentlik, LLP

(57) ABSTRACT

Devices and systems provide methods of detecting a heart failure condition of a patient that may be based on one or more respiratory parameters of a patient. In an example embodiment, a monitoring device determines one or more heart failure condition indicators based on a measure of the patient respiratory airflow and/or a measure of treatment pressure. Respiratory parameters such as respiration rate, hypopneas, apneas, Cheyne-Stokes breathing patterns or apnea-hypopnea counts may be compared to thresholds that are selected to represent a change in the condition of a heart failure patient such as an onset of a decompensation event. Results of the comparisons may trigger a pressure treatment change and/or one or more warnings or messages to notify a patient or physician of a pending change to the patient's heart failure condition so that the patient may more immediately seek medical attention to treat the heart failure condition.

44 Claims, 6 Drawing Sheets

(56) References Cited

U.S. PATENT DOCUMENTS

| | | | |
|---|---|---|---|
| 5,188,098 A | | 2/1993 | Hoffman et al. |
| 5,259,373 A | * | 11/1993 | Gruenke et al. ......... 128/204.23 |
| 5,353,788 A | | 10/1994 | Miles |
| 5,535,738 A | | 7/1996 | Estes et al. |
| 5,584,290 A | | 12/1996 | Brain |
| 5,704,345 A | | 1/1998 | Berthon-Jones |
| 5,740,797 A | | 4/1998 | Dickson |
| 5,794,615 A | | 8/1998 | Estes |
| 5,846,720 A | | 12/1998 | Foulkes et al. |
| 6,105,575 A | | 8/2000 | Estes et al. |
| 7,100,608 B2 | | 9/2006 | Brewer et al. |
| 7,210,478 B2 | * | 5/2007 | Banner et al. ............ 128/204.23 |
| 7,398,115 B2 | * | 7/2008 | Lynn ............................ 600/324 |
| 7,575,005 B2 | * | 8/2009 | Mumford et al. ........ 128/205.23 |
| 8,251,061 B2 | * | 8/2012 | Lee et al. ................. 128/204.23 |
| 2002/0088465 A1 | | 7/2002 | Hill |
| 2002/0169384 A1 | | 11/2002 | Kowallik et al. |
| 2003/0078619 A1 | | 4/2003 | Bonnet et al. |
| 2003/0121519 A1 | | 7/2003 | Estes et al. |
| 2003/0154979 A1 | | 8/2003 | Berthon-Jones |
| 2004/0134496 A1 | | 7/2004 | Cho et al. |
| 2004/0237963 A1 | | 12/2004 | Berthon-Jones |
| 2005/0121033 A1 | | 6/2005 | Starr et al. |
| 2006/0241510 A1 | | 10/2006 | Halperin et al. |
| 2007/0129643 A1 | | 6/2007 | Kwok et al. |
| 2007/0135724 A1 | | 6/2007 | Ujhazy et al. |
| 2008/0000475 A1 | | 1/2008 | Hill |
| 2010/0018530 A1 | | 1/2010 | Schindhelm et al. |

FOREIGN PATENT DOCUMENTS

| | | |
|---|---|---|
| WO | 89-09041 A1 | 10/1989 |
| WO | 8909041 A1 | 10/1989 |
| WO | 96/32055 A1 | 10/1996 |
| WO | 97-30744 A1 | 8/1997 |
| WO | 98/52467 A1 | 11/1998 |
| WO | 99-45989 A1 | 9/1999 |
| WO | 99-61088 A1 | 12/1999 |
| WO | 00-45702 A1 | 8/2000 |
| WO | 00-67827 A1 | 11/2000 |
| WO | 0067827 A1 | 11/2000 |
| WO | 2002-026283 A2 | 4/2002 |
| WO | 2005/037355 A1 | 4/2005 |
| WO | 2006-037184 A1 | 4/2006 |
| WO | 2006/066337 A1 | 6/2006 |

OTHER PUBLICATIONS

Examination Report from Corresponding NZ Application No. 578601, dated Jul. 31, 2009.

* cited by examiner

METHOD AND APPARATUS FOR DETECTING AND TREATING HEART FAILURE

CROSS-REFERENCE TO RELATED APPLICATIONS

This application claims the benefit of the filing date of U.S. Provisional Patent Application No. 61/083,596, filed Jul. 25, 2008, the disclosure of which is hereby incorporated herein by reference.

FIELD OF THE TECHNOLOGY

The present technology relates to methods and apparatus for detecting and treating the condition of heart failure.

BACKGROUND OF THE TECHNOLOGY

Heart Failure or Congestive Heart Failure affects approximately five million Americans. CHF is characterized by the Medline Encyclopedia as a life-threatening condition in which the heart can no longer pump enough blood to meet the demands of the body. Heart failure is almost always a chronic, long-term condition, although it can sometimes develop suddenly. This condition may affect the right side, the left side, or both sides of the heart. As the heart's pumping action is lost, blood may back up into other areas of the body, including:
  the liver;
  the gastrointestinal tract and the extremities (right-sided heart failure); and
  the lungs (left-sided heart failure).

With heart failure, many organs do not receive enough oxygen and nutrients. This damages the organs and reduces their ability to function properly. Most areas of the body may be affected when both sides of the heart fail.

A common cause of heart failure is hypertension (i.e., high blood pressure). Another common cause of heart failure is coronary artery disease (e.g., a heart attack). Other structural or functional causes of heart failure include:
  Valvular heart disease;
  Congenital heart disease;
  Dilated cardiomyopathy;
  Lung disease; and
  Heart tumor.

Heart failure is more common with advancing age. Risk factors for developing heart failure include being overweight, having diabetes, smoking cigarettes, abusing alcohol, or using cocaine.

There are devices that may be useful in diagnosing a patient's heart failure condition. For example, imaging tools may be used. In this regard, echocardiography is commonly used to support a clinical diagnosis of heart failure. This analysis uses ultrasound to determine a stroke volume ("SV"). A stroke volume is an amount of blood in the heart that exits the ventricles with each beat. The analysis may also determine an end-diastolic volume ("EV") or total amount of blood at the end of diastole. The analysis may also be used to determine the SV in proportion to the EV. This proportion is a value known as the ejection fraction ("EF"). In pediatrics, the shortening fraction is the preferred measure of systolic function. Normally, the EF should be between 50% and 70%. However, in systolic heart failure, the EV typically drops below 40%. Echocardiography may also be used to identify valvular heart disease and assess the state of the pericardium (i.e., the connective tissue sac surrounding the heart). Echocardiography may also aid in deciding what treatments will help the patient, such as medication, insertion of an implantable cardioverter-defibrillator or cardiac resynchronization therapy.

Chest X-rays are another frequently used tool for diagnosing CHF. In the compensated patient, this may show cardiomegaly (a visible enlargement of the heart), quantified as the cardiothoracic ratio (a proportion of the heart size to the chest). In left ventricular failure, there may be evidence of vascular redistribution ("upper lobe blood diversion" or "cephalization"), Kerley lines, cuffing of the areas around the bronchi, and interstitial edema.

An electrocardiogram (ECG/EKG) may be used to identify arrhythmias, ischemic heart disease, right and left ventricular hypertrophy, and presence of conduction delay or abnormalities (e.g. left bundle branch block). These results may be evaluated in making a diagnosis of heart failure.

Blood tests may also be used to diagnose the condition. For example, measures of electrolytes (sodium, potassium), measures of renal function, liver function tests, thyroid function tests, a complete blood count, and often C-reactive protein if an infection is possible, may be used to diagnose the patient's condition. One specific test for heart failure determines the level of B-type natriuretic peptide (BNP). An elevated level of BNP may suggest the existence of heart failure. The BNP level may differentiate heart failure as a cause of dyspnea from other conditions that may cause dyspnea. If myocardial infarction is a possibility, cardiac markers may be used in the diagnosis of heart failure.

A patient's heart failure condition may be the result of coronary artery disease. The condition may depend on the ability of the coronary arteries to provide blood to the myocardium. Thus, a coronary catheterization may also help to identify possibilities for revascularization through percutaneous coronary intervention or bypass surgery.

Different measures may be determined to assess the progress of a patient's heart failure condition. A fluid balance or calculation of fluid intake and excretion can assist in monitoring a patient's condition. Similarly, changes in body weight, which may reflect fluid shifts, can be considered.

There is no present gold standard in the diagnosis of heart failure. The Framingham criteria, which was derived from the Framingham Heart Study, the Boston criteria, the Duke criteria and the Killip classification are systems that are commonly considered in evaluating a patient for heart failure.

A functional classification of heart failure may also be considered by classes defined by the New York Heart Association Functional Classification (NYHAFC). A score according to this classification system grades the severity of symptoms, and can be used to assess the patient's responses to treatment. While it is commonly used, the NYHAFC score may not be reliably reproducible.

The classes (I-IV) of the NYHAFC system are:
  Class I: no limitation is experienced in any activities; there are no symptoms from ordinary activities.
  Class II: slight, mild limitation of activity; the patient is comfortable at rest or with mild exertion.
  Class III: marked limitation of any activity; the patient is comfortable only at rest.
  Class IV: any physical activity brings on discomfort and symptoms occur at rest.

In its 2001 guidelines, the American College of Cardiology/American Heart Association working group introduced four stages of heart failure:
  Stage A: a high risk HF in the future but no structural heart disorder;
  Stage B: a structural heart disorder but no symptoms at any stage;

Stage C: previous or current symptoms of heart failure in the context of an underlying structural heart problem, but managed with medical treatment;

Stage D: advanced disease requiring hospital-based support, a heart transplant or palliative care.

It will be appreciated that there is a need in the art for improved techniques and devices for addressing the conditions of heart failure.

BRIEF SUMMARY OF THE TECHNOLOGY

An aspect of certain example embodiments of the present technology relates to a system for detecting the presence of, or a change in condition (e.g., worsening) of Congestive Heart Failure. In one form this involves an apparatus for determining and monitoring a respiratory parameter of a patient. For example, the apparatus monitors a change in the pattern of apneas and/or hypopneas of a patient and/or a change in Cheyne-Stokes breathing. The apparatus may determine a change or worsening of a condition of the patient upon an increase in the number and/or duration of apneas, hypopneas and/or Cheyne-Stokes breathing.

In some embodiments of the technology, a method involves evaluating a heart failure condition of a patient by measuring a respiratory airflow of the patient and then determining a heart failure condition change indicator based on the respiratory airflow. The indicator represents information about a heart failure condition of the patient.

In some embodiments of the technology, a system monitors a patient to evaluate a heart failure condition of a patient. A typical system may include a patient interface and a flow sensor coupled thereto. The flow sensor generates a respiratory airflow signal representative of the patient's respiratory airflow from the patient interface. A processor of the system is configured to control a determination of the heart failure condition indicator based on data from the respiratory airflow signal.

In still other embodiments of the technology, a device or apparatus monitors a patient to evaluate a heart failure condition of a patient. The apparatus or device may include a patient respiratory interface with a sensor coupled with the patient interface. The sensor generates a signal representative of the patient's respiratory airflow. A processor, which may be coupled with the flow sensor, controls a determination of a heart failure condition indicator based on the respiratory airflow signal.

In one or more of the above embodiments, a warning signal, warning light or warning message may be generated to inform a patient/user of the technology and/or a physician treating the patient. The warning signals, warning lights or messages of the embodiments may be generated and transmitted between devices to permit remote monitoring and notification of the patient's heart failure condition. The warning signals, warning light and/or warning messages will typically be triggered by the evaluation of the heart failure condition indicators.

Some embodiments of the present technology involve a method for evaluating a heart failure condition of a patient during respiratory pressure treatment. The method may include determining a measure of treatment pressure delivered by a respiratory treatment apparatus with a sensor. It may further include determining a heart failure condition change indicator with a processor based on the measure of pressure. The method may still further include determining a measure of respiration of the patient with a sensor, wherein the determining of the heart failure condition change indicator is further based on the respiration measure. The determining of the indicator may optionally include a threshold comparison that detects an increase in a proportion of the measure of pressure and an increase in an apnea or AHI count during a common time period. In some embodiments, the method may also involve controlling of a change to a pressure treatment therapy of a respiratory treatment apparatus in response to one or more determined indicators. This change in control may optionally involve initiating control of ventilation support to meet a target ventilation.

Similarly, some embodiments may involve an apparatus for evaluating a heart failure condition of a patient during respiratory pressure treatment. The apparatus may include a sensor to determine a measure of treatment pressure delivered by a respiratory treatment apparatus. A processor of the apparatus may determine a heart failure condition change indicator based on the measure of pressure. The processor may also be configured to determine a measure of respiration of the patient with data from a sensor so that the processor can determine the heart failure condition change indicator based on the respiration measure. Optionally, the processor may implement a threshold comparison that detects an increase in a proportion of the measure of pressure and an increase in an apnea or AHI count during a common time period. In some embodiments, the apparatus may include a flow generator coupled with the processor such that the processor may be configured to control a change to a pressure treatment therapy of the respiratory treatment apparatus in response to the determined indicator. Such a change may be initiating control of ventilation support to meet a target ventilation.

Various aspects of the described example embodiments may be combined with aspects of certain other example embodiments to realize yet further embodiments.

Other features of the technology will be apparent from consideration of the information contained in the following detailed description.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION

The present technology involves methods and devices for the treatment of patients at risk for heart failure or congestive heart failure or changes in the condition of these diseases. For example, some heart failure patients suffer congestive heart failure exacerbation. Congestive heart failure exacerbation is also known as decompensated heart failure (DHF). Typically, acute decompensation results in pulmonary oedema. Treatment of this condition will typically require hospitalization for the patient. However, if the potential for acute decompensation is caught early enough, such as at the earliest stages of the onset of pulmonary oedema, it may be treated in a manner that does not require hospitalization. The heart failure condition indicator of the devices of the present technology provides a basis for detecting such changes in congestive heart failure and for notifying the patient or medical providers of the potential need for medical intervention with respect to the heart failure condition of the patient.

Figure 1:
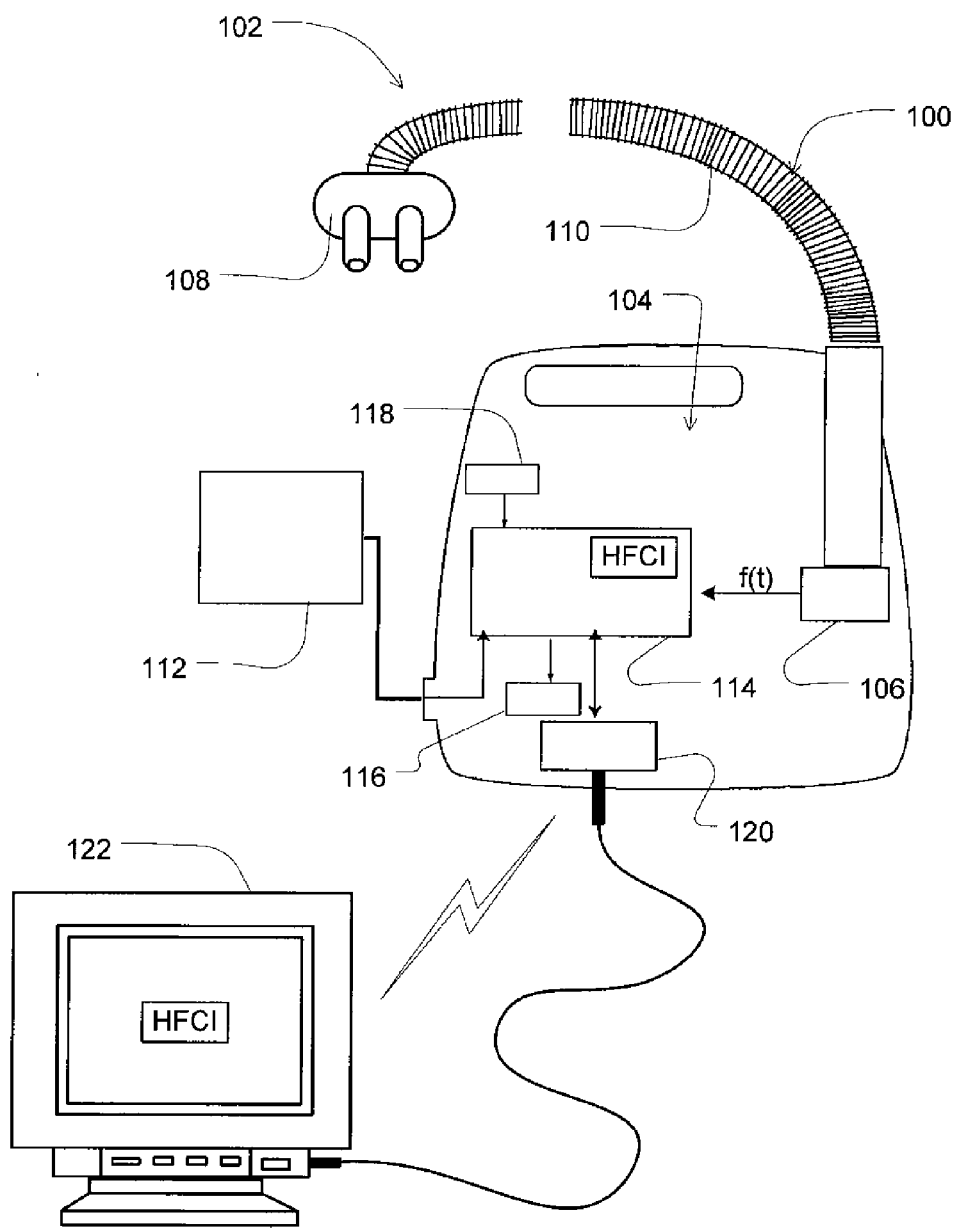
FIG. 1 illustrates example components of a monitoring device to implement a heart failure condition indicator.

One embodiment of a device for implementing one or more of the heart failure condition indicators of the present technology is illustrated in FIG. 1. In the embodiment, the heart failure detection device 100 implements a heart failure condition change indicator (referenced in FIG. 1 as "HFCI"). The heart failure detection device 100 will typically include a patient respiratory interface 102, a controller 104 and a flow sensor 106. The patient respiratory interface, which will typically include a cannula 108 and/or sense tube 110, receives and/or senses airflow from the patient's respiratory system via the patient's mouth and/or the patient's nares. Alternatively, the patient respiratory interface may be implemented with a nasal mask, nose & mouth mask, full-face mask or nasal pillows.

The flow sensor 106 may be coupled with the patient respiratory interface. The flow sensor generates a signal representative of the patient's respiratory flow. For example, flow proximate to the nasal cannula 108 or sense tube 110 may be measured using a pneumotachograph and differential pressure transducer or similar device such as one employing a bundle of tubes or ducts to derive a flow signal f(t). Alternatively, a pressure sensor may be implemented as a flow sensor and a flow signal may be generated based on the changes in pressure. Although the flow sensor 106 is illustrated in a housing of the controller 104, it may optionally be located closer to the patient, such as in the nasal cannula 108 or sense tube 110. Other devices for generating a respiratory flow signal may also be implemented.

Optionally, the heart failure detection device 100 may also include additional diagnosis sensors 112. For example, the device may include an oximeter. The oximeter may generate a signal representative of a blood oxygen level of a patient. A suitable example oximeter or monitor device may optionally be any of the devices disclosed in International Patent Application No. International Application No. PCT/AU2005/001543 (Pub. No. WO/2006/037184) or International Patent Application No. PCT/AU1996/000218 (Pub. No. WO/1996/032055), the disclosures of which are incorporated herein by cross-reference. As disclosed in these incorporated PCT applications, the monitor may serve as diagnosis sensors that can also optionally provide a blood pressure and/or pulse rate monitor for measuring a pulse rate and/or blood pressure of the patient.

In some embodiments, the diagnosis sensors may also include an ECG monitor such as the LifeScreen Apnea monitor provided by BiancaMed. Such a device may be configured to detect cardiac-related characteristics (e.g., ECG signals) and determine respiratory parameters (such as central or obstruction apneas, hypopneas, etc.) and other parameters (e.g., arrhythmias) that may be experienced by the patient by analyzing the ECG signals from the patient. Optionally, these parameters may be determined by the analysis algorithms of controller 104 based on transmission of the ECG data to the controller or they may be determined by the monitor and be transmitted to the controller 104.

In still further embodiments, the diagnosis sensors may also or alternatively include an ultrasonic screening sensor for detecting obstructive or central apneas by non-contact sensing. For example, the sensor may monitor sound such as by the use of ultrasonic sensors to detect obstructive or central apneas, hypopneas and other respiratory parameters from the signals measured by the sensors. Such non-contact based measures may then be implemented for monitoring of the patient's condition as discussed in more detail herein. Thus, the data from the sensors may be transmitted to the controller 104 for use and analysis by the controller. Such a sensor may be implemented in a heart failure detection device of the present technology without the use of a contact-based sensor or without the use of a mask or cannula that may otherwise be used with a flow sensor for a more direct measure of patient airflow. Thus, in this embodiment no patient intervention is required for the diagnosis sensing.

In some embodiments, the diagnosis sensors may include a movement sensor. For example, a suprasternal notch sensor or chest band may be implemented to generate a movement signal that is indicative of patient respiration. Other suitable sensors may include the movement sensing devices disclosed in International Patent Application No. PCT/AU1998/000358 (Pub. No. WO/1998/052467), the disclosure of which is incorporated herein by cross-reference. The movement sensors thus may provide a measure of patient respiration and may be used as an alternative to a flow sensor or in conjunction with other flow sensors in the determination of respiratory parameters as discussed herein.

The signals from the sensors may be sent to the controller 104. Optional analog-to-digital (A/D) converters/samplers (not shown separately) may be utilized in the event that supplied signals from the sensors are not in digital form and the controller is a digital controller. Based on the signals from the sensor(s), the controller assesses the changing heart failure condition of the patient with one or more heart failure condition indicators HFCI.

The controller may optionally include a display device 116 such as one or more warning lights (e.g., one or more light emitting diodes). The display device may also be implemented as a display screen such as an LCD. Activation of the display device 116 will typically be set by the controller based on an assessment of the particular heart failure condition change indicators implemented by the heart failure detection device 100. The display device may be implemented to visually show information to a user of the heart failure detection device 100 or a clinician or physician. The display device 116 may also show a graphic user interface for operation of the heart failure detection device 100. User, clinician or physician control of the operation of the heart failure detection device 100 may be based on operation of input switches 118 that may be sensed by the controller or processor.

Optionally, the controller may also include a communications device 120 for receiving and/or transmitting data or messages by the heart failure detection device 100. For example, the communications device may be a wireless transceiver such as Bluetooth or WIFI transceiver. The communications device may also be a network communications device such as a phone modem and/or network card and may be implemented to send messages via the internet directly or through a computer to which the heart failure detection device may be docked. In general, the communications device 120 may be used to transmit warnings or messages to a clinician or physician assessable apparatus 122 such as a multi-patient monitoring system that allows a physician to review data from remote patient data recording devices such as the heart failure detection device 100. In these systems, a database is provided to record patient monitoring data. Physicians or clinicians may receive a report, or warning that the patient may require closer observation, or should be brought to hospital.

The controller 104 will also typically include a processor 114 configured to implement particular control methodology such as the algorithms described in more detail herein. Thus, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium. With such a controller or processor, the device can be used for determining and analyzing many different parameters associated with the patient's condition based on data from the sensors. Thus, the processor may control the assessment of a heart failure condition indicator HFCI or heart failure condition change indicator as described in the embodiments discussed in more detail herein.

Figure 2:
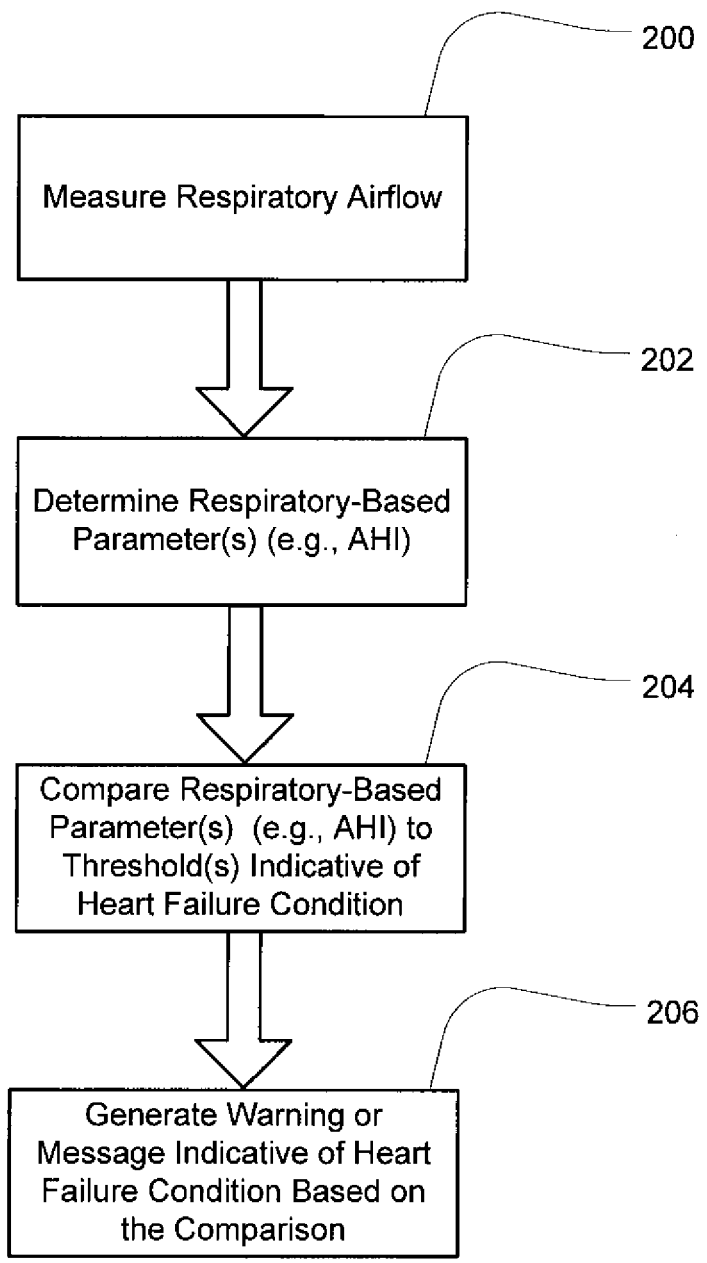
FIG. 2 is an example methodology for a device that implements a heart failure condition indicator for detecting a condition of heart failure patients.

One example methodology or algorithm of the controller 104 of the heart failure detection device 100 is illustrated in the flow chart of FIG. 2. Generally, the heart failure detection device 100 may monitor respiratory-related characteristics such as the patient respiratory airflow with at least one of the flow sensors or a respiratory-related characteristic deriving device as previously described. For example, in step 200 the respiratory airflow of the patient may be measured and provided to a processor of the controller.

Based on the analysis algorithms implemented in the controller 104, the heart failure detection device will then determine one or more respiratory-based parameters from the measure of respiratory airflow or other sensor data in step 202.

For example, a respiratory parameter may be a respiratory rate, number of apneas, a number of hypopneas or an Apnea-Hypopnea Index (AHI). To this end, based on the continuous airflow signal from the sensors and/or other sensor input, the processor may analyze patterns of patient data, such as patterns of the airflow signal, patterns of an ECG signal, etc., to detect occurrences of apneas and/or hypopneas. Methods and apparatus for detecting apneas and hypopneas are described in U.S. Pat. No. 5,704,345, the contents of which are hereby incorporated herein by cross-reference. An "apnea" may be considered a cessation of breathing by the patient for more than 10 seconds. A hypopnea may be defined as a reduction in ventilation to between about 30% to about 70% of normal ventilation. The AHI may be calculated as the number of apneas and hypopneas in a particular time period such as an hour, in a day or during a particular sleep session. Other forms of an AHI may also be implemented.

Other respiratory-based parameters may also be determined. For example, the processor may also be configured to determine a number of Cheyne-Stokes breaths during a particular time interval such as an hour, in a day or a particular sleep session. One suitable measure may be the detection of a number of Cheyne-Stokes epochs. An example methodology for a detection of Cheyne-Stokes epochs from a flow signal is described in International Patent Application No. PCT/AU2005/001942 (Pub. No. WO/2006/066337), the disclosure of which is hereby incorporated herein by cross-reference. Optionally, or alternatively, other sensors may be utilized to detect events of Cheyne-Stokes Respiration (CSR) for implementation with the heart failure change indicators of the present technology. For example, oximetry may be utilized to assess a presence of CSR.

In step 204, the controller 104 will then compare one or more of the determined respiratory parameters and/or patient parameters to one or more thresholds. Typically, each threshold is chosen so that the results of the comparison indicate a change in the heart failure condition of the patient such as the patient beginning to experience an onset of acute decompensation. For example, a determined respiratory parameter such as the AHI may be compared to a prior AHI for the patient or an average AHI for the patient from a previous time frame, such as one or more prior monitoring sessions. A present change to the AHI (such as an increase or a decrease or a certain amount of increase or decrease) over a previous determined AHI may be taken as a heart failure condition change indicator. For example, an increase of ten or more may be considered indicative of a change in the heart failure condition of the patient. More complex thresholds indicative of changes in the AHI may also be assessed as the heart failure condition change indicator. For example, increases in the AHI for two or more consecutive days of monitoring sessions may be taken as the heart failure condition change indicator HFCI. Furthermore, the thresholds may be selected to consider how significant the change or increases are in AHI such as ignoring small changes or small increases (e.g., 2 or fewer).

Alternately, or in addition, a heart failure change indicator may be based on the determined Cheyne-Stokes breathing patterns or epochs and one or more thresholds. For example, a count of Cheyne-Stokes epochs from a current session may be taken as the respiratory parameter and may be compared to a prior count of Cheyne-Stokes epochs for the patient or an average number of epochs for the patient from a previous time frame, such as one or more prior monitoring sessions. A present change to the epoch count (such as an increase or a decrease or a certain amount of increase or decrease) over a previous determined epoch count may be taken as a heart failure condition indicator. Still more complex thresholds indicative of changes in the epoch may also be assessed as the heart failure condition indicator. For example, increases in the epochs for two or more consecutive days of monitoring sessions without a comparable decrease over the same consecutive day time frame in the following days may be taken as the heart failure condition indicator.

Optionally, a heart failure indicator may be based on the results of the comparison of several thresholds and several respiratory parameters or patient parameters. For example, an increase in the AHI over several sessions coupled with an increase in the Cheyne-Stokes epoch count over several sessions may collectively be taken as a heart failure condition change indicator.

In some embodiments, one or more of the heart failure condition indicators may also be based on a threshold comparison involving measures of heart rate, blood pressure and/or blood-oxygen levels. In an example of such an embodiment, a measured ratio of $O_2$ to $CO_2$ as it changes over time may be compared to a threshold such as a prior measure of the ratio. A certain level of change in the measure may be considered a heart failure change indicator. Still other patient parameters or measures may also be implemented as a heart failure change indicator with the present technology. Suitable examples may include heart-rate variability metrics (e.g., measures of sympathovagal balance), cardio pulmonary coupling (e.g., correlation of pulse and breathing), arterial $CO_2$ tension (e.g., non-invasive estimate via trans-cutaneous $CO_2$ or end-tidal $CO_2$) and/or one or more photoploethysmogram-derived indices (e.g., relative respiratory effort and/or variation thereof, arterial stiffness, cardiopulmonary coupling, HRV, etc.).

Moreover, one or more of these patient parameters or measures may be compared with one or more thresholds. The results of one or more of these comparisons may then serve as a heart failure change indicator or may be combined with one or more other respiratory-based parameters to serve as a heart failure condition change indicator. For example, a decrease in an average pulse rate of a patient over several sessions combined with an increase in a number of epochs during the same sessions may be taken as a heart failure condition indicator.

Thresholds associated with these patient parameters such as the respiratory-based parameters may be determined through empirical analysis of the conditions and changes experienced by congestive heart failure patients.

An apparatus or device in accordance with the invention provides a convenient way to monitor patients and may even be utilized while they sleep. Thus, in optional step 206 of FIG. 1, when the device determines that a change in the patient's condition is a worsening state of the patients heart based on the heart failure condition indicators HFCI, the heart failure condition change indicators may be used to trigger the device to provide a warning or message in a form suitable for the patient and/or clinicians to be aware of the status of the patient's heart so that the patient may more efficiently receive the care that is necessary.

The warning or messaging of the system may take a number of forms. For example, the controller, in response to an affirmative heart failure condition change indicator, may activate a status light (e.g., an LED or an icon on a display screen or LCD) of the monitoring device. A more detailed message concerning the assessment of the indicator may also be displayed on the display screen. Optionally, the controller may also, or alternatively, send a message to a clinician of physician. Such a message may take the form of a wired or wireless communication. For example, the controller may generate a message via a paging system such as by automatically dialing a paging system. The controller may also be configured to generate an automated voice phone call message. The controller may also send the message by a fax transmission. In some embodiments, the controller may also send a message via any internet messaging protocol, such as an email message, or by any other internet data file transport protocol. The messages may even be encrypted to keep patient information confidential. A typical message may identify the patient. Such a message may also include the data of the changes recorded by the system any other recorded patient information. The message may even express that the patient should be considered for additional heart failure treatment or an evaluation due to the detection of a potential decompensation event.

Thus, an example embodiment of a display or warning that may be presented to a patient or physician by the device may be a warning message such as a graphic or textual message. The message may be displayed on the device or a remote device based on the evaluation of one or more of the programmed heart failure condition change indicators HFCI. For example, the warning message may be based on an increase in the measured Cheyne-Stokes epochs count (e.g., an increase of more than 20 units or some other number of units from a set of previous days counts (e.g., two days)). The warning message may also be based on an increase in the AHI index (e.g., an increase by more than 10 units or some other number of units from a set of previous days indices (e.g., two days)). Such a heart failure condition indicator(s) could trigger the message(s). Still optionally, the message may also be based on a collective combination of the two example increases such that the message is triggered only when both conditions are met.

While a simple warning message may be utilized, graded levels of warning messages may also be generated to describe the patient's heart failure condition as multiple different heart failure condition indicators or a repeated heart failure condition indicator collectively triggers the different messages based on the severity of the detected conditions. For example, one heart failure condition indicator may trigger an initial warning message on a certain day. However, a different message, such as one with a higher level of urgency, may be generated by a second and different heart failure condition indicator on a subsequent day based on the previously illustrated collective condition that involves both the AHI and the Cheyne-Stokes epoch respiratory parameters. In such an embodiment, after the first message, the second message may more urgently warn that the patient should immediately contact a physician for a medical examination. In this manner, the device may monitor or store data concerning each warning so that the warnings may be progressively altered or generated based on prior warnings and/or heart failure change indicators.

Furthermore, while all of these messages could be directed by the controller 104 to the patient via the display device 116 of the heart failure detection device 100 and the physician via the communications device 120, in some embodiments, the messages could be directed more selectively. For example, the first message may be only transmitted to a physician or clinician by only transmitting the message to a physician system 122 through the communications device 120 without showing it on the display device 116. However, the second message, which may be a more urgent message, could then be actively displayed on the display device 116 in addition to transmitting it to the physician system 122. An audible alarm from an optional speaker controlled by the controller of the device may also be implemented. Use of an audible alarm may depend on the urgency of the message.

While the heart failure condition indicator technology may be included in a monitoring device such as the heart failure detection device 100, the technology may also be combined with other devices. For example, the technology may be implemented in devices used for monitoring other patient conditions. Thus, the technology may be implemented in such diagnosis or screening devices as the APNEA LINK (ResMed), EMBLETTA (Flaga), RUSleeping™ (Respironics) and the E-series (Compumedics) etc. Optionally, it may be implemented with a non-contact sleep monitoring device such as a non-contact AHI screener (e.g., BiancaMed biomotion sensor, which detects movement, respiration, respiratory effort, and/or heart rate via low power pulses of radio frequency energy.)

By way of further example, the heart failure detection device may be implemented in respiratory treatment devices. Thus, the technology may be implemented in automatic diagnosis and treatment devices such as the ResMed AUTOSET series of devices including the AUTOSET CS, and adaptive servo ventilation devices, such as the ResMed VPAP Adapt SV. For example, FIG. 3 illustrates a respiratory treatment device that may implement the technology described herein.

Figure 3:
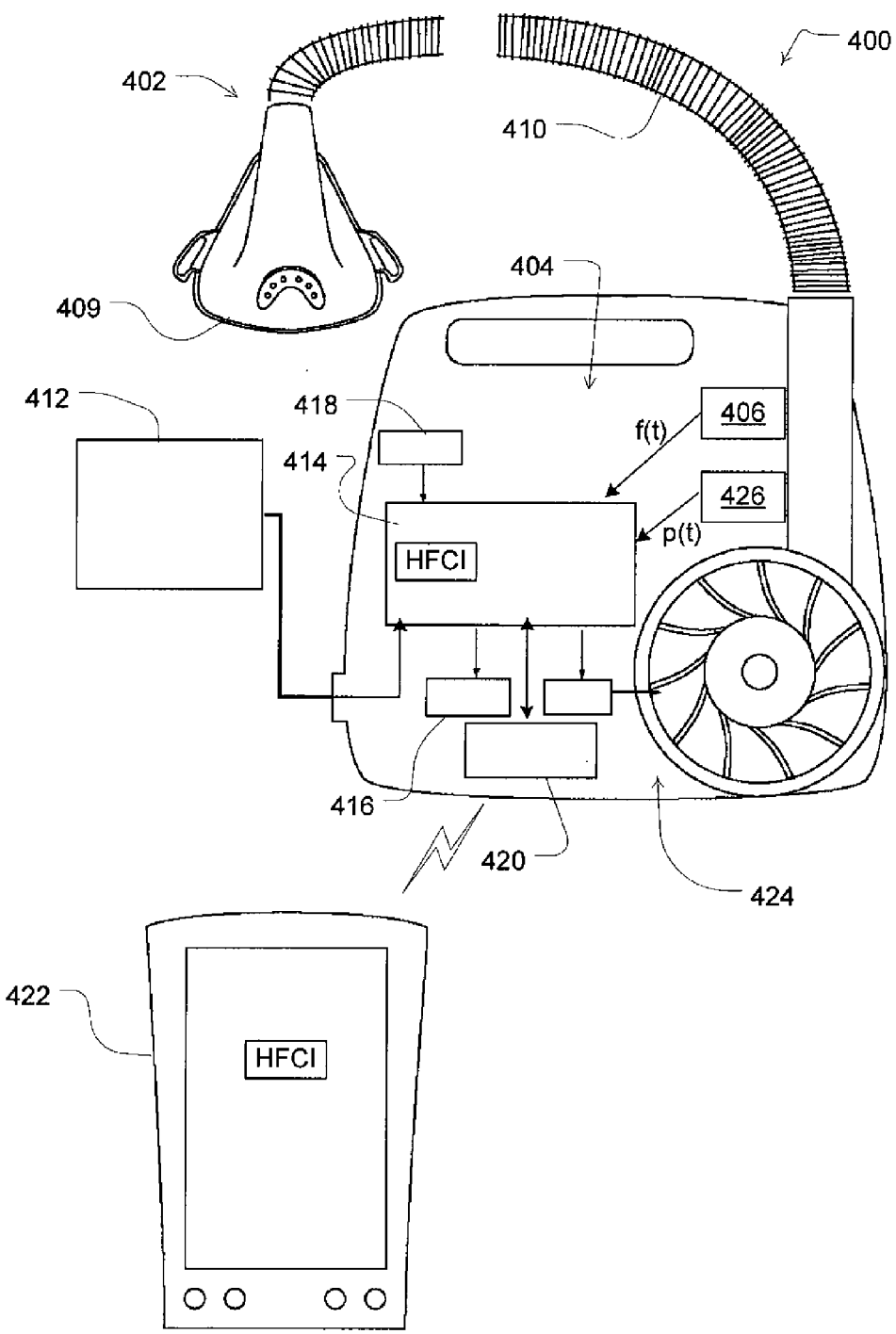
FIG. 3 illustrates a further monitoring device with additional components for delivering a pressure treatment therapy to the patient.

In reference to FIG. 3, the monitoring and treatment device 400 may serve as the heart failure detection device 100. Thus, the device may include a patient respiratory interface 402, such as a mask 409 and delivery tube 410, like the device of FIG. 1. In such a device, the delivery tube 410 may serve as the sense tube 110. The monitoring and treatment device may also include a flow sensor 406, a controller 404, display device 416, switches 418, communications device 420 and diagnosis sensors 412 comparable to the components previously described with respect to the device of FIG. 1. The device may also communicate generated messages to the physician system 422 as previously discussed.

However, the monitoring and treatment device 400 of FIG. 3 may also optionally be configured to provide a respiratory pressure treatment from a flow generator such as a servo-controlled blower 424. The device may further include a pressure sensor 106, such as a pressure transducer to measure the pressure generated by the blower 102 and generate a pressure signal p(t) indicative of the measurements of pressure.

Based on flow f(t) and pressure p(t) signals, the controller 404 with a processor 414 generates blower control signals. For example, the controller may generate a desired pressure set point and servo-control the blower to meet the set point by comparing the setpoint with the measured condition of the pressure sensor. Thus, the controller 404 may make controlled changes to the pressure delivered to the patient interface by the blower 102. Optionally, such changes to pressure may be implemented by controlling an exhaust with a mechanical release valve (not shown) to increase or decrease the exhaust while maintaining a relatively constant blower speed. With such a controller or processor, the apparatus can be used for many different pressure treatment therapies, such as the pressure treatments for sleep disordered breathing, Cheyne-Stokes Respiration or obstructive sleep apnea (e.g., CPAP, APAP, Bi-Level CPAP, Auto-VPAP, etc.) by adjusting a suitable pressure delivery equation.

Figure 4:
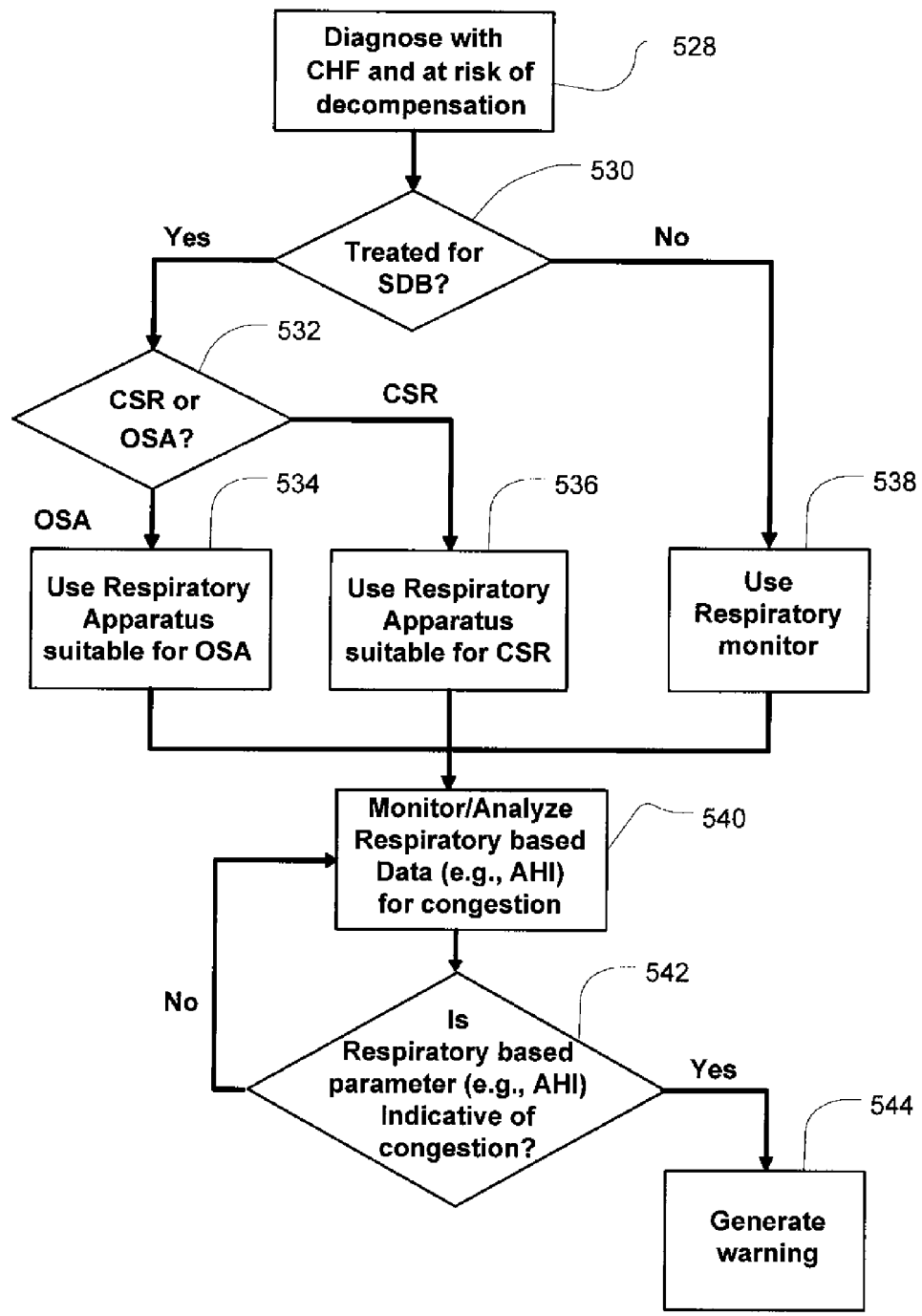
FIG. 4 is an example diagnosis flowchart for implementing treatment with devices that incorporate the heart failure condition indicator of the present technology.

To this end, an example clinical methodology for prescribing and using some embodiments of the present technology is illustrated in FIG. 4. In step 528, a patient is diagnosed with congestive heart failure and may be at a risk of experiencing acute decompensation. In step 530, the patient is evaluated for Sleep Disordered Breathing (SDB) or determined if the patient is being treated for SDB. If the patient does not have this condition, the patient may be provided a heart failure treatment device 100 in step 538 for use, such as during the patient's sleep. Alternatively, in step 530 if the patient does have Sleep Disordered Breathing, the patient may be evaluated for Cheyne-Stokes Respiration (CSR) or Obstructive Sleep Apnea (OSA). In the former case, the patient would be provided a device capable of generating treatment pressures for addressing CSR in step 536. Alternatively, in the latter case of OSA, the patient would be provided a device capable of generating treatment pressures for addressing OSA in step 534. In step 540, each of the devices would monitor and analyze information based on the patient's respiration to determine the respiratory based parameters as previously discussed with respect to the algorithm of FIG. 2. In step 542, the thresholds of one or more heart failure condition indicators would be evaluated. If a heart failure condition indicator suggests that the patient is experiencing a worsening or change of the heart failure conduction such as a decompensation event, a warning would be triggered in step 544. However, if the heart failure condition indicators do not suggest the presence of such a change in condition, no warning would be generated and the device would continue to monitor and analyze by returning to step 540. In this way, the present technology may be realized in different devices depending on the needs of the patient while taking advantage of the existing components of other devices that the patient may need.

Figure 5:
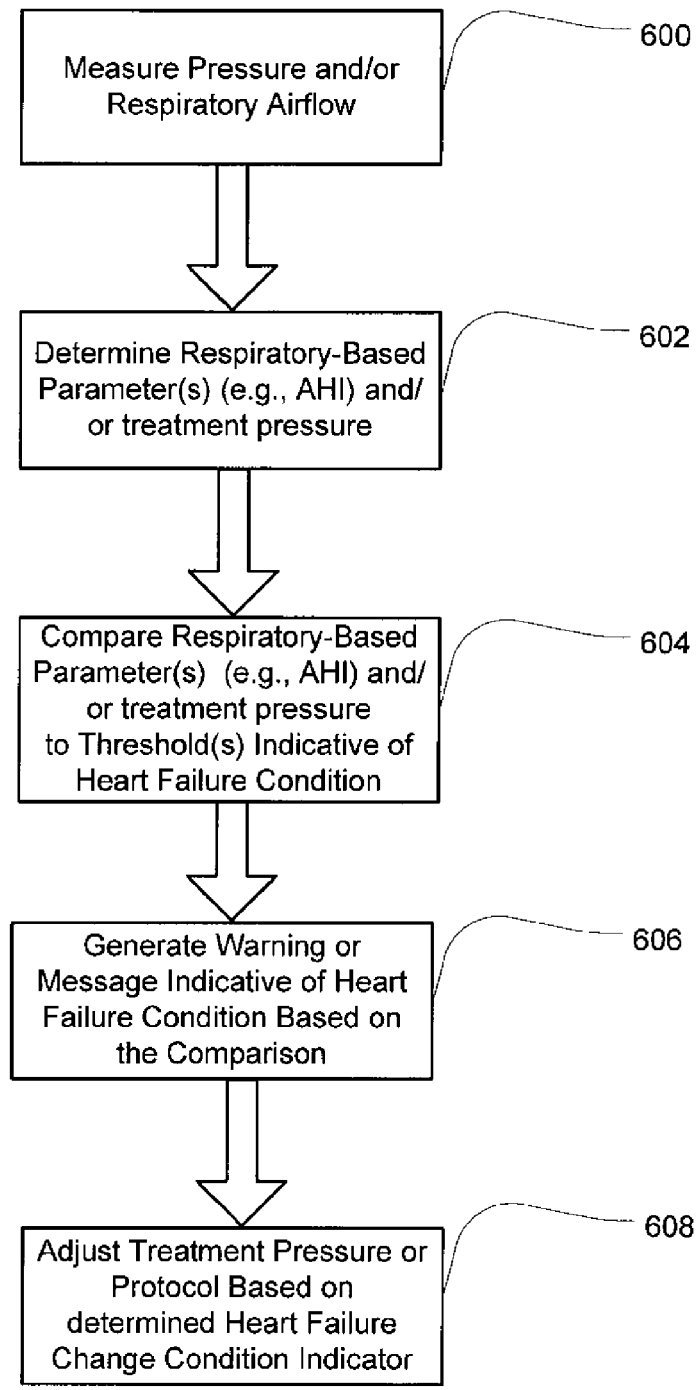
FIG. 5 is another example methodology for a device that implements a heart failure condition indicator for detecting a condition of heart failure patients.

In some embodiments of the present technology as illustrated in FIG. 5, the assessed heart failure condition indicator may also be based on a measure of pressure associated with a respiratory treatment generated by a treatment apparatus such as, for example, an adaptive servo ventilator or other respiratory treatment device that detects and responds to respiratory events such as central apneas, hypopneas and/or obstructive apneas (e.g., an auto-titrating SDB apparatus, auto-end expiratory pressure (EEP) setting apparatus and/or a device that measures ventilation and maintains a target ventilation). Thus, in 600, pressure may be measured by a sensor of a respiratory treatment apparatus such as an adaptive servo-ventilator. In 602, treatment pressure may then be determined based on the pressure measure. Example treatment pressure measures may include a peak inspiratory pressure, proportion of delivered pressure treatment, median pressure, and/or a level of pressure support, etc. These measures may be determined by the device on a session by session basis or some other time period. For example, such a measure may be determined by monitoring a 95th percentile pressure delivered during a treatment session as described in U.S. Pat. No. 7,100,608 assigned to ResMed Ltd. and filed on Jan. 4, 2002, the entire disclosure of which is incorporated herein by cross-reference. Such measures may be monitored and compared to one or more suitable thresholds to provide a heart failure condition indication in 604. The history of such measures may be considered over days or months. For example, one or more of these measures and suitable threshold(s), such as a certain amount of change in one or more sessions when compared to one or more prior sessions may serve as the indicator. Thus, the indicator may be based on a recent trend indicating increases in one or more pressure measures from a prior period of time or prior treatment session or sessions and may result in the triggering of a warning in 608.

Figure 6:
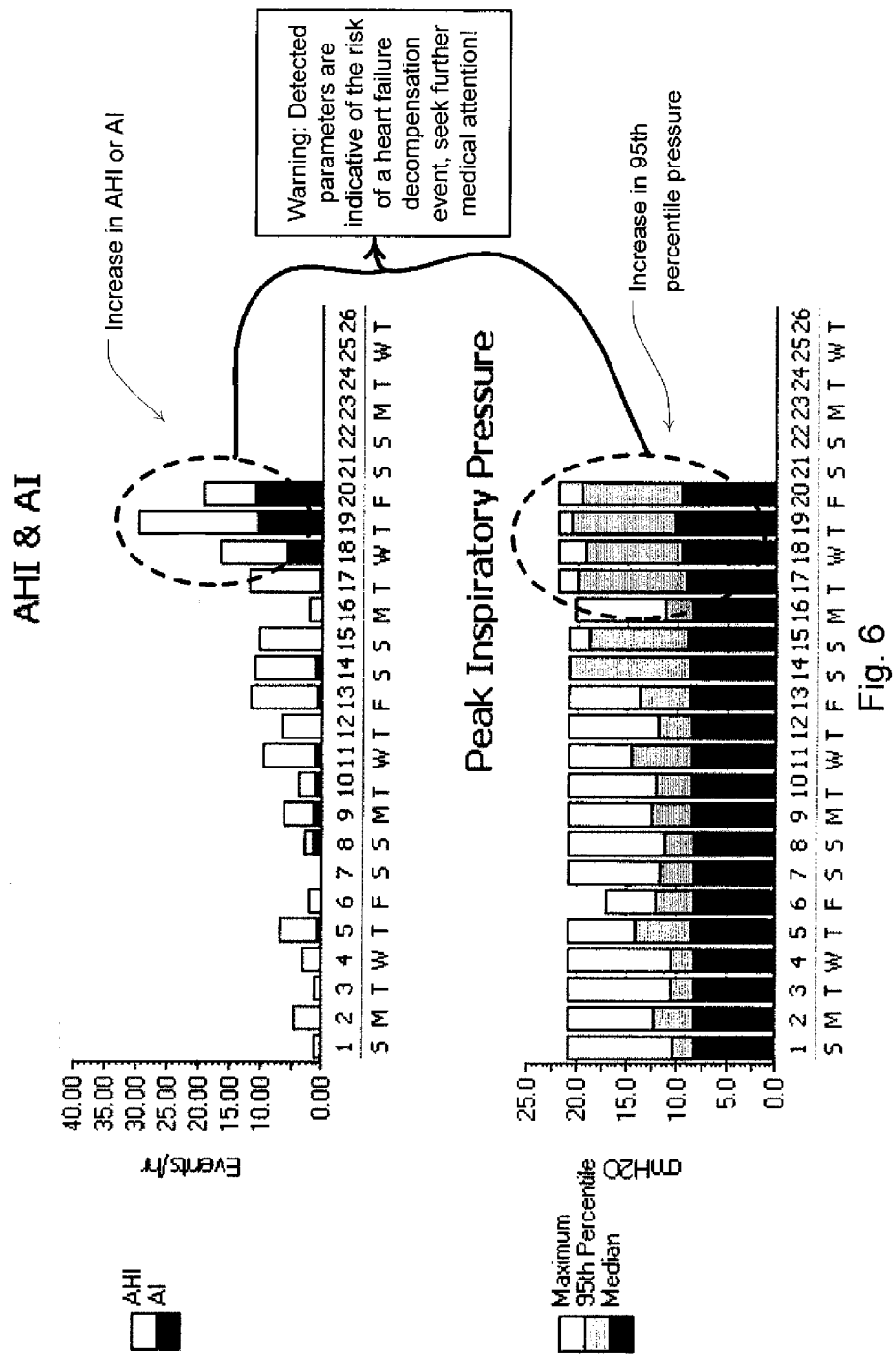
FIG. 6 illustrates and example warning message based on an example heart failure condition indicator of the present technology.

These indicators may also be combined with other indicators previously discussed to yield a sophisticated and synergistic early warning of decompensation events. For example, the indicator based on an increase or a trend of increases in pressure may be combined with an indicator based on changes in an apnea and/or hypopnea count during a common set of treatment sessions. For example, a moderate or small increase or increasing trend in an AHI and/or an apnea count (shown as "AI" in FIG. 6) (e.g., obstructive apnea and/or central apnea) by an amount coupled with an increase or an increasing trend in a treatment pressure measure may serve as a combined heart failure condition indicator if detected during a similar time period. Such a warning that may be generated by a device based on a several session increase in both $95^{th}$ percentile pressure and either AHI or AI is illustrated in FIG. 6. As also illustrated, the device may optionally generate a report showing or illustrating the analyzed measures that are associated with the particular heart failure change indicator.

In some embodiments, the positive indication of a detection of decompensation from one or more heart failure condition indicators may be implemented to control an automated change in a treatment therapy provided by a respiratory treatment apparatus as illustrated at 608 in FIG. 5. For example, upon a positive indication, the treatment control methodology of the device may modify control of the flow generator to change a pressure response of the device. For example, a modification in treatment therapy protocol may be implemented. In one such embodiment, the change in control may cause the respiratory treatment apparatus to begin to control pressure changes so that a measure of ventilation meets a target ventilation. For example, a processor of a treatment apparatus may servo-control the flow generator to deliver a pressure treatment that satisfies the target ventilation. A target ventilation may be predetermined by a physician or automatically set with a learning mode of a respiratory treatment device. Such a device will typically measure delivered ventilation and adjust the pressure being supplied to the patient in a manner to ensure that the measured ventilation satisfies the target ventilation. Thus, if a patient's respiration causes the measured ventilation to begin to fall below or rise above the target ventilation over time, the flow generator will compensate with an increase or decrease respectively in the supplied pressure support. In this way, an automatically setting SDB device (e.g., an auto-titrating CPAP or Bi-level device) may begin to function as a servo-controlled ventilator in response to the detection of one or several decompensation events. Optionally, other changes to the pressure control or pressure settings may be implemented in response to a positive or negative indication of one or more heart failure condition indicators. For example, a negative indication subsequent to a positive indication may return the pressure treatment control protocol from a ventilation target enforcing protocol to an auto-titrating SDB protocol. By way of further examples, positive indications of decompensation may be implemented to control a modification of the target for ventilation enforcement. For example, the target may be increased based on additional detections of decompensation. In one such embodiment, a device which enforces a calculated target ventilation (e.g., 90% of a long term ventilation measure) may change its target to a predetermined (e.g., clinician prescribed) and recorded target ventilation such as an estimate of gross alveolar ventilation.

While the heart failure condition indicator technology has been described in several embodiments, it is to be understood that these embodiments are merely illustrative of the technology. Further modifications may be devised within the spirit and scope of this description.

For example, while an integrated device is contemplated by the present technology, the methodology of the components of the devices may be shared across multiple components of a system. For example, a monitoring device may simply measure the respiratory data of the patient and transfer the data to another processing system. The second processing system may in turn analyze the respiration data to determine the respiratory parameters used in an analysis of the present technology. The second processing system may also evaluate the heart failure condition indicators and generate warning messages as described herein, such as by sending one or more of the described messages, in electronic form for example, back to the patient monitoring device for display on the device to warn the patient.

By way of further example, in some embodiments, the apparatus or system may also determine a change that is representative of improvement of a heart failure condition of the patient. For example, a decrease in the number and/or duration of apneas, hypopneas, Cheyne-Stokes breathing and/or any other determined change to any respiratory parameters and/or patient parameters may serve as one or more heart failure condition indicators as previously discussed. A suitable message may then be generated based thereon to inform the user and/or physician of the potential need to revise the patient's medical treatment (e.g., a reduction in heart failure related medication, reduction or change in pressure treatment or pressure treatment protocol, etc.) due to the patient's improvement. In some embodiments, the detected improvement may even serve as a control to a change in treatment such as, for example, a change to a pressure treatment setting or a pressure treatment protocol of a respiratory treatment apparatus. For example, an indication of improvement may control a change from a protocol that delivers respiratory support to maintain a ventilation target to one that does not, such as a SDB device that treats Cheyne-Stokes Respiration or obstructive sleep apnea (e.g., CPAP, APAP, Bi-Level CPAP or other device that detects apnea and/or obstructive events and sets a treatment pressure to treat the detected event.)

Other variations can be made without departing with the spirit and scope of the technology.

The invention claimed is:

1. A device for monitoring a patient to evaluate a heart failure condition of a patient comprising:
a patient interface;
a non-invasive sensor to generate a signal associated with a characteristic of patient respiration; and
a processor, coupled with the sensor, the processor configured to control and store a determination of a heart failure condition change indicator based on the signal, compare previously stored and determined values of the indicator from one or more previous treatment sessions and determine a risk of a heart failure decompensation event occurring for the patient based on the comparison, wherein the processor is further configured to trigger a heart failure decompensation risk message based on the comparison.

2. The device of claim 1 wherein a determination of a heart failure condition change indicator is based on a threshold comparison that involves a respiratory rate determined from the signal of the non-invasive sensor.

3. The device of claim 2 further comprising a sensor to generate a signal representative of a respiratory treatment pressure, and
wherein a determined heart failure condition change indicator is based on (a) an additional respiratory parameter determined from the respiration measure and (b) a determined treatment pressure, wherein the additional respiratory parameter is an apnea-hypopnea count or apnea count.

4. The device of claim 1 wherein the processor activates a warning based on the heart failure condition change indicator.

5. The device of claim 4 wherein the warning comprises a light signal or a message.

6. The device of claim 4 wherein the message comprises an electronic message to be transmitted.

7. The device of claim 1 further comprising a transmitter coupled with the processor, wherein the processor is further configured to control transmitting of a message including data representing the heart failure condition indicator.

8. The device of claim 1 further comprising a flow generator coupled to the processor and the patient interface, wherein the processor is configured to control generating a flow of breathable gas at a pressure above atmospheric to the patient interface.

9. The device of claim 1 wherein the processor is configured to determine a heart failure condition change indicator with a plurality of threshold comparisons involving a plurality of respiratory parameters determined from a measure of respiratory airflow and wherein the characteristic of respiration is the measure of respiratory airflow.

10. The device of claim 9 wherein the respiratory parameters comprise data representative of one or more apneas and hypopneas experienced by the patient and data representative of one or more Cheyne-Stokes epochs experienced by the patient.

11. The device of claim 1 wherein the processor is configured to determine the heart failure condition change indicator with a threshold comparison involving an oximetry measure and wherein the characteristic of respiration is the oximetry measure.

12. The device of claim 1 further comprising an ultrasonic sensing device and wherein the processor is configured to determine a heart failure condition change indicator based on data determined by the ultrasonic sensing device.

13. The device of claim 1 wherein the processor is configured to determine a heart failure condition change indicator based on a determined heart-rate variability metric.

14. The device of claim 1 wherein the processor is configured to determine a heart failure condition change indicator based on a measure of sympathovagal balance.

15. The device of claim 1 wherein the processor is configured to determine a heart failure condition change indicator based on a measure of gas of a patient's blood.

16. The device of claim 15 further comprising a photoplethysmograph to derive the measure of gas.

17. An apparatus for monitoring a patient to evaluate a heart failure condition of the patient comprising:
sensor means for non-invasively determining a measure of a respiration characteristic of the patient;
respiration analysis means for determining a respiratory parameter based on the measure generated by the sensor means; and
analysis means for evaluating at least the respiratory parameter to generate and store a heart failure condition change indicator based on a signal from the sensor means, to compare previously stored and determined values of the indicator from one or more previous treatment sessions and determine a risk of a heart failure decompensation event occurring for the patient based on the comparison, wherein the analysis means is further configured to trigger a heart failure decompensation risk message based on the comparison.

18. The apparatus of claim 17 further comprising means for transmitting a message representing the heart failure condition change indicator.

19. The apparatus of claim 17 further comprising means for warning a user of the system based on the heart failure condition change indicator.

20. The apparatus of claim 17 further comprising a means for delivering pressurized breathable gas to the patient.

21. The apparatus of claim 17 further comprising means for warning a physician of the system based on the heart failure condition change indicator.

22. A system for monitoring a patient to evaluate a heart failure condition of a patient comprising:
a patient interface;
a non-invasive flow sensor coupled with the patient interface, the flow sensor to generate a respiratory airflow signal representative of the patient's respiratory airflow; and
a processor configured to control and store a determination of a heart failure condition change indicator based on data from the respiratory airflow signal, compare previously stored and determined values of the indicator from one or more previous treatment sessions and determine a risk of a heart failure decompensation event occurring for the patient based on the comparison, wherein the processor is further configured to trigger a heart failure decompensation risk message based on the comparison.

23. The system of claim 22 wherein a determination of a heart failure condition change indicator is based on a respiratory rate determined from the respiratory airflow signal.

24. The system of claim 23 further comprising a sensor to generate a signal representative of a respiratory treatment pressure, and wherein a determined heart failure condition change indicator is based on (a) an additional respiratory parameter determined from the respiratory airflow and (b) a determined treatment pressure, wherein the additional respiratory parameter is an apnea-hypopnea count or apnea count.

25. The system of claim 22 wherein the processor activates a warning based on the heart failure condition indicator.

26. The system of claim 25 wherein the warning comprises a light activation signal.

27. The system of claim 25 wherein the warning comprises an electronic message to be transmitted, the message including data representing the heart failure condition change indicator.

28. The system of claim 22 further comprising a flow generator coupled to the patient interface, wherein the flow generator is configured to generate a flow of breathable gas at a pressure above atmospheric to the patient interface.

29. The system of claim 22 wherein the processor is configured to determine a heart failure condition indicator with a plurality of threshold comparisons involving a plurality of respiratory parameters determined from the measure of respiratory airflow.

30. The system of claim 29 wherein the respiratory parameters comprise data representative of one or more apneas and hypopneas experienced by the patient and data representative of one or more Cheyne-Stokes epochs experienced by the patient.

31. The system of claim 22 further comprising an ultrasonic sensing device and wherein the processor is configured to determine a heart failure condition change indicator based on data determined by the ultrasonic sensing device.

32. The system of claim 22 wherein the processor is configured to determine a heart failure condition change indicator based on a determined heart-rate variability metric.

33. The system of claim 22 wherein the processor is configured to determine a heart failure condition change indicator based on a measure of sympathovagal balance.

34. The system of claim 22 wherein the processor is configured to determine a heart failure condition change indicator based on a measure of gas of a patient's blood.

35. The system of claim 34 further comprising a photoplethysmograph to derive the measure of gas.

36. An apparatus for evaluating a heart failure condition of a patient during respiratory pressure treatment comprising:
a sensor to determine a measure of treatment pressure delivered by a respiratory treatment apparatus; and
a processor coupled with the sensor, the processor configured to control a determination of a heart failure condition change indicator based on changes in the measure of pressure over time, the indicator representing information about a change in a heart failure condition of the patient.

37. The apparatus of claim 36 wherein the processor is configured to determine a measure of respiration of the patient with data from a sensor; and
wherein the processor is configured to determine the heart failure condition change indicator based on the respiration measure.

38. The apparatus of claim 37 wherein the processor implements a threshold comparison that detects an increase in a proportion of the measure of pressure and an increase in an apnea or AHI count during a common time period.

39. The apparatus of claim 38 further comprising a flow generator coupled with the processor and wherein the processor is configured to control a change to a pressure treatment therapy of the respiratory treatment apparatus in response to the heart failure condition change indicator.

40. The apparatus of claim 39 wherein the change to the pressure treatment therapy comprises initiating control of ventilation support to meet a target ventilation.

41. A device for monitoring a patient to evaluate a heart failure condition of a patient comprising:
a patient interface;
a non-invasive sensor to generate a signal associated with a characteristic of patient respiration, wherein the non-invasive sensor is an ultrasonic sensing device;

a processor, coupled with the sensor, the processor configured to control a determination of a heart failure condition change indicator based on the characteristic of respiration, the indicator representing information about a change in a heart failure condition of the patient, wherein the respiratory parameter is respiratory rate, and wherein the processor is configured to perform a threshold comparison of the respiratory parameter determined by the processor, a result of the comparison triggers a heart failure condition message, and the processor is configured to determine a heart failure condition change indicator based on data determined by the ultrasonic sensing device.

42. A device for monitoring a patient to evaluate a heart failure condition of a patient comprising:

a patient interface;

a non-invasive sensor to generate a signal associated with a characteristic of patient respiration;

a processor, coupled with the sensor, the processor configured to control a determination of a heart failure condition change indicator based on the characteristic of respiration, the indicator representing information about a change in a heart failure condition of the patient, wherein the respiratory parameter is respiratory rate, wherein the processor is configured to perform a threshold comparison of the respiratory parameter determined by the processor, a result of the comparison triggers a heart failure condition message, and the processor is configured to determine a heart failure condition change indicator based on a determined heart-rate variability metric.

43. A system for monitoring a patient to evaluate a heart failure condition of a patient comprising:

a patient interface;

a non-invasive flow sensor coupled with the patient interface, the flow sensor to generate a respiratory airflow signal representative of the patient's respiratory airflow;

a processor configured to control a determination of a heart failure condition change indicator based on data from the respiratory airflow signal, the indicator representing information about a change in a heart failure condition of the patient; and an ultrasonic sensing device, wherein the processor is configured to perform a threshold comparison of a respiratory rate parameter determined from the data by the processor, a result of the comparison triggers a heart failure condition message, and the processor is configured to determine a heart failure condition change indicator based on data determined by the ultrasonic sensing device.

44. A system for monitoring a patient to evaluate a heart failure condition of a patient comprising:

a patient interface;

a non-invasive flow sensor coupled with the patient interface, the flow sensor to generate a respiratory airflow signal representative of the patient's respiratory airflow;

a processor configured to control a determination of a heart failure condition change indicator based on data from the respiratory airflow signal, the indicator representing information about a change in a heart failure condition of the patient, wherein the processor is configured to perform a threshold comparison of a respiratory rate parameter determined from the data by the processor, a result of the comparison triggers a heart failure condition message, and the processor is configured to determine a heart failure condition change indicator based on a determined heart-rate variability metric.

* * * * *